(12) United States Patent
Rohde et al.

(10) Patent No.: US 7,157,411 B2
(45) Date of Patent: Jan. 2, 2007

(54) ODOR NEUTRALIZERS

(75) Inventors: Ute Rohde, Höxter (DE); Stephan Hillers, Holzminden (DE); Horst Surburg, Holzminden (DE); Steffen Sonnenberg, Holzminden (DE); Keith McDermott, Bound Brook, NJ (US); Leslie Smith, Princeton, NJ (US); Karl Sparkuhle, Holzminden (DE)

(73) Assignee: Symrise GmbH & Co. KG, Holzminden (DE)

( * ) Notice: Subject to any disclaimer, the term of this patent is extended or adjusted under 35 U.S.C. 154(b) by 0 days.

(21) Appl. No.: 10/149,564

(22) PCT Filed: Dec. 8, 2000

(86) PCT No.: PCT/EP00/12374

§ 371 (c)(1),
(2), (4) Date: Sep. 9, 2002

(87) PCT Pub. No.: WO01/43784

PCT Pub. Date: Jun. 21, 2001

(65) Prior Publication Data

US 2003/0068295 A1   Apr. 10, 2003

(51) Int. Cl.
*C11D 3/50* (2006.01)
(52) U.S. Cl. .............................. 510/106; 512/22
(58) Field of Classification Search ............... 560/205, 560/231; 512/23; 510/106
See application file for complete search history.

(56) References Cited

U.S. PATENT DOCUMENTS 3,607,651 A * 9/1971 Moroe et al. ............... 435/280

(Continued)

FOREIGN PATENT DOCUMENTS

DE    4441463 A1 * 6/1995

(Continued)

OTHER PUBLICATIONS

Chem. Abstract 111:176823 & JP 01056798, "Liquid detergent-bleach compositions containing perfume." Koichi Kishida et al.
Chem. Abstract 128:326350 & JP 10120541, "Deodorant cosmetics containing free perfumes and cyclodextrin-perfume inclusion compounds." Ayako Fujimoto et al.

(Continued)

*Primary Examiner*—John R. Hardee
(74) *Attorney, Agent, or Firm*—Stephan Pendorf; Akerman & Senterfit

(57) ABSTRACT

This invention relates to odor neutralizers comprising esters of the formula (I) wherein $R^1$ is an alkyl radical with 1 to 4 carbon atoms which can optionally contain a double bond; $R^2$ is a hydrogen or an alkyl radical with 1 to 3 carbon atoms which can optionally contain a double bond; $R^3$ is a hydrogen or a methyl radical substituted by the alkyl radicals $R^9$ and $R^{10}$; $R^4$ is a hydrogen, a methyl radical or an acyloxy radical of the general formula O—CO—$R^1$ wherein $R^1$ has the abovementioned meaning; $R^5$, $R^6$, $R^7$, $R^8$ and $R^{10}$ are identical or different and is hydrogen or methyl; $R^9$ is a hydrogen and $R^4$ and $R^9$ can together represent a single carbon bond or a methylene or an ethylene bridge, with the proviso that i) in the case of cyclohexyl esters in which $R^1$=methyl, $R^2$=isopropyl, $R^5$=methyl and $R^6$=hydrogen, the substituents $R^2$ and $R^5$ are arranged in a cis relationship to each other; ii) in the case of cyclohexyl esters in which $R^2$=isopropenyl, $R^5$=methyl and $R^6$=hydrogen, the substituent $R^1$ is an alkyl group with at least two C atoms; iii) in the case of acyclic monofunctional esters, the substituent $R^1$ is an alkyl group with at least two C atoms; and iv) in the case of cyclohexyl esters in which $R^2$, $R^7$, $R^8$=hydrogen and $R^5$, $R^6$, $R^{10}$=methyl, the substituent $R^1$ is methyl, ethyl, propyl or 1-propen-1-yl.

6 Claims, 1 Drawing Sheet

U.S. PATENT DOCUMENTS

| | | | |
|---|---|---|---|
| 3,620,918 A | * 11/1971 | Moroe et al. | 435/155 |
| 4,009,253 A | 2/1977 | Schleppnik et al. | 424/45 |
| 4,719,105 A | 1/1988 | Schleppnik | 424/76.21 |
| 5,023,020 A | * 6/1991 | Machida et al. | 261/18.1 |
| 5,355,718 A | * 10/1994 | Mookherjee et al. | 73/23.34 |
| 5,380,707 A | 1/1995 | Barr et al. | 512/17 |
| 5,501,805 A | 3/1996 | Behan et al. | 252/8.6 |
| 5,559,271 A | 9/1996 | Shaw et al. | 568/21 |
| 5,676,163 A | 10/1997 | Behan et al. | 131/213 |
| 5,683,979 A | 11/1997 | Schreck et al. | 512/13 |
| 5,789,010 A | 8/1998 | Behan et al. | 426/534 |

FOREIGN PATENT DOCUMENTS

| | | | |
|---|---|---|---|
| EP | 0 411 460 | | 2/1991 |
| FR | 1516938 | * | 3/1968 |
| GB | 1545561 | | 5/1979 |
| JP | 50-74581 | * | 6/1975 |
| WO | 95/21606 | | 8/1995 |
| WO | 96/31590 | | 10/1996 |
| WO | WO 97/15283 | * | 5/1997 |
| WO | 99/18940 | | 4/1999 |

OTHER PUBLICATIONS

Chem. Abstract 119:187285 & JP 05058869, "Admixtures for preventing generation of offensive odor form cement mortar and concrete." Yoji Watanabe et al.

Chem. Abstract 110:140763 & JP 2726846, "Deodorization of respiratory air." Kuniharu Takami et al.

Chem. Abstract 107:238946 & JP 03029280. "Aromatic liquid bleaching agent compositions." Yu Izumio et al.

Chem. Abstract 105:29193 & HU 36383. Compositions for modifying the organoleptic threshold value of odorants, as well as for reducing the sensitivity of the odor sensing human/animal nerves.

Chem. Abstract 102:225585 & JP 03044781, "Fragrant deodorizing mixtures." Ogawa and Co., Ltd., Japan.

Database WPI Section Ch, Week 198645 Derwent Publication Ltd., London, GB; AN 1986-295737 XP002168514 & JP 61 218543 A (Taiyo Koryo KK), Sep. 29, 1986 abstract.

Database WPI Section Ch, Week 198526 Derwent Publications Ltd., London, GB; AN 1985-156593 XP002168515 & JP 60 088558 A (Hasegawa Co Ltd), May 18, 1985 abstract.

* cited by examiner

ODOR NEUTRALIZERS

FIELD OF THE INVENTION

The invention relates to odor neutralizers and their use for masking malodors.

BACKGROUND OF THE INVENTION

In many applicational areas, perfumes are used for masking malodors. Annoyance caused by malodors occurs frequently in daily life and impairs personal well-being. Such malodors are, for example, those resulting from substances transpired or excreted by humans, in particular, perspiration, feces and urine, odors caused by animal feces or urine, in particular, those of domestic pets, kitchen odors, such as those resulting from the preparation of onions, garlic, cabbage or fish, odors due to tobacco smoke, and in particular, cold tobacco smoke, molds and waste.

In addition, malodors are caused by many industrially produced basic materials used in cleansing agents, such as, for example, detergents and fabric softeners, or in body care products, such as, for example, soaps and cosmetics. The use of specific cosmetic preparations, such as, for example, hair dyes, hair-forming agents and depilatories, also produce malodors.

Many rubber and plastic products also produce malodors if, due to the method of their manufacture, they still contain quantities of highly odorous, volatile active ingredients.

These malodors are usually caused by particularly odorous substances which are, however, frequently only present in trace amounts. Such substances include, for example, nitrogen-containing compounds such as ammonia and amines, heterocyclic compounds such as pyridines, pyrazines, indoles, etc. and sulfur-containing compounds such as hydrogen sulfide, mercaptans, sulfides, etc.

The masking of malodors is a problem, which is difficult to handle and solve with perfume compositions. The specific unique quality of a malodor greatly restricts the use of perfumes having the various types of commonly known fragrances. Usually, it is only possible to mask malodors by means of a specially developed perfume oil having a very specific type of fragrance.

Active ingredients are, therefore, particularly advantageous when they are capable of reducing the intensity of malodors without themselves possessing any significantly intense odor or fragrance. Such active ingredients do not mask malodors but neutralize them. This has the advantage that when using such active ingredients for perfuming objects or products with malodors, perfume oils of any desired type of fragrance can be used. The consumer can, therefore, be offered a considerably broader range of fragrance types for combating malodors.

In addition, active ingredients, which neutralize malodors, provide the possibility of reducing the quantity of perfume oil previously required for masking odors. It is also possible to use less intensely odorous perfumes for combating malodors than those so far employed, which sometimes have an overpowering effect due to their high intensity.

U.S. Pat. No. 5,676,163 describes the use of aldehydes employed as perfumes for combating malodors caused by nitrogen-containing active ingredients contained in tobacco smoke.

U.S. Pat. No. 5,501,805 describes the reduction of malodors with the aid of selected perfume raw materials such as, for example, musk perfumes and salicylates.

EP A 780132 describes combating malodors using a combination of musk and citrus perfumes and peppermint oil.

U.S. Pat. No. 4,719,105 describes the use of cyclohexyl methanols and esters thereof, preferably, for use in air fresheners for combating various malodors.

U.S. Pat. No. 4,009,253 describes the use of 4-cyclohexyl-4-methyl-2-pentanone for combating malodors.

U.S. Pat. No. 5,789,010 describes reducing unpleasant aldehyde odors in triglycerides by adding an amine and masking the odor by adding a perfume aldehyde.

WO 96/31590 describes masking the odor of bleaching liquids with the aid of selected perfume raw materials.

JP B 01056798 (cf Chem. Abstr. 111, 176823) also describes masking the odor of bleaching liquids with the aid of selected perfumes, such as, for example, 2,6-di-methyl-4-heptyl acetate and 3,3,5-trimethylcyclohexyl isobutyrate.

U.S. Pat. No. 5,380,707 describes combating body odor using a musk perfume.

In Patents Nos. JP A 10120541 (cf. Chem. Abstr. 128, 326350), U.S. Pat. No. 5,559,271, JP A 05058869 (cf. Chem. Abstr. 119, 187285), JP A 2726846 (cf. Chem. Abstr. 110, 140763), JP A 03029280 (cf Chem. Abstr. 107, 238946), HU 36383 (cf. Chem. Abstr. 105, 29193) and JP A 03044781 (cf Chem. Abstr. 102, 225585) menthyl acetate or 1-menthyl acetate are described as ingredients of perfume mixtures which are suitable for combating malodors of the most varied kinds. In WO 98/27261 1-isopulegyl acetate is also mentioned as an odor-combating agent in addition to menthyl acetate.

The known agents for masking or neutralizing malodors only act in specific cases and thus, restrict the perfume manufacturer's means of combination.

SUMMARY OF THE INVENTION

Therefore, there is an urgent need for additional active ingredients with the above properties so that the present situation of limited usability can be improved and the range of possible uses broadened.

Odor neutralizers have been found which contain esters of the formula

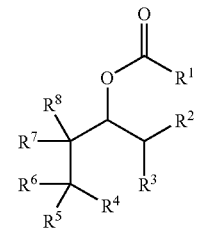

wherein $R^1$ is an alkyl radical with 1 to 4 carbon atoms which can optionally contain a double bond;

$R^2$ is a hydrogen or an alkyl radical with 1 to 3 carbon atoms which can optionally contain a double bond;

$R^3$ is a hydrogen or a methyl radical substituted by the alkyl radicals $R^9$ and $R^{10}$;

$R^4$ is a hydrogen, a methyl radical or an acyloxy radical of the general formula $$O-CO-R^1$$

wherein $R^1$ has the abovementioned meaning;

$R^5$, $R^6$, $R^7$, $R^8$ and $R^{10}$ are identical or different and is hydrogen or methyl;

$R^9$ is a hydrogen and $R^4$ and $R^9$ can together represent a single carbon bond or a methylene or an ethylene bridge, with the proviso that
  i) in the case of cyclohexyl esters in which $R^1$=methyl, $R^2$=isopropyl, $R^5$=methyl and $R^6$=hydrogen, the substituents $R^2$ and $R^5$ are arranged in a cis relationship to each other;
  ii) in the case of cyclohexyl esters in which $R^2$=isopropenyl, $R^5$=methyl and $R^6$=hydrogen, the substituent $R^1$ is an alkyl group with at least two C atoms;
  iii) in the case of acyclic monofunctional esters, the substituent $R^1$ is an alkyl group with at least two C atoms; and
  iv) in the case of cyclohexyl esters in which $R^2$, $R^7$, $R^8$=hydrogen and $R^5$, $R^6$, $R^{10}$=methyl, the substituent $R^1$ is methyl, ethyl, propyl or 1-propen-1-yl.

DETAILED DESCRIPTION OF THE INVENTION

Figure 1:
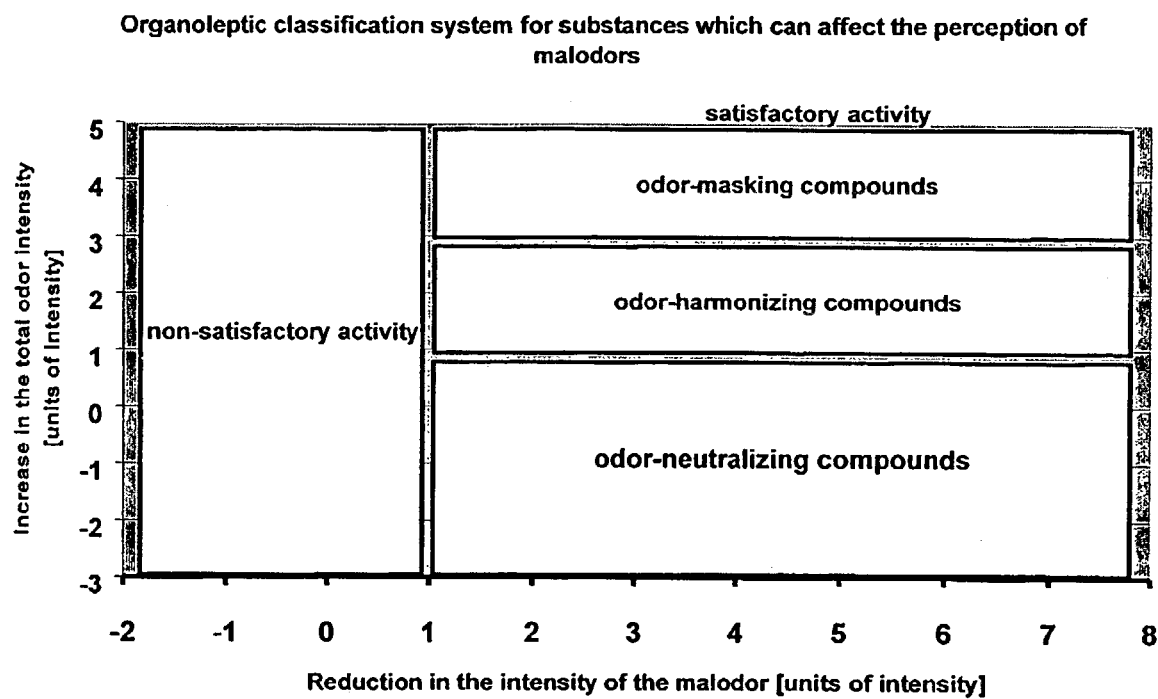
FIG. 1 shows a table of an organoleptic classification system for substances which can affect the perception of malodors.

The esters act as active ingredients in the odor neutralizers according to the present invention. In contrast to odor-masking or odor-harmonizing compounds, odor neutralizers can be identified for practical use by the following analytical method:

In a vessel suitable for detecting odors, small quantities of a test mixture producing a malodor are mixed with small quantities of the test substance. The odor of the gas phase above the samples in the vessel is compared with that of the gas phase of another vessel which only contains the test mixture having the malodor.

The assessments are carried out by a panel of organoleptically trained experts. The degree of offensiveness of the malodor is given values between 0 and 10 (0=no odor; 10=extremely odorous). In addition, the total odor intensity is assessed in the same manner, in order to determine whether the malodor is indeed reduced or only masked.

The capacity of volatile compounds for reducing the intensity of malodors varies greatly. A large number of such compounds are not capable at all of affecting the perception of malodors. As shown in FIG. 1, compounds which reduce the intensity of malodors by at least one unit of intensity can however be subdivided into the following three categories:
  1. If the compounds increase the total odor intensity by more than three units of intensity, such compounds constitute perfumes which mask the malodor as a result of their own powerful pleasant odor; they include a large number of conventional perfume raw materials ("odor-masking compounds").
  2. Compounds which increase the total odor intensity by at most three and at least one unit of intensity are so-called "odor-harmonizing compounds". These are usually conventional perfume raw materials which do not have such an intense inherent odor. These compounds are on a level between odor-masking compounds and odor neutralizers. They reduce malodors but have a characteristic inherent odor.
  3. Compounds which increase the total odor intensity only by at most one unit of intensity or even reduce same are so-called "odor neutralizers". They are capable of reducing the perception of malodors without themselves leaving any dominant odor impression.

It is clear from the above-description that the neutralizers are the most valuable substances for combating malodors. In contrast to odor-masking and odor-harmonizing compounds, the use of neutralizers is not tied to specific types or kinds of fragrance; they can therefore be universally applied.

The property of the esters according to the present invention of neutralizing malodors is surprising.

The preferred odor neutralizers used are those comprising esters of the formula

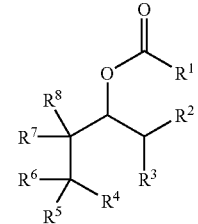

wherein
$R^1$ is methyl, ethyl, 2-propyl or 1-propen-1-yl;
$R^2$ is a hydrogen, methyl or 2-propyl;
$R^3$ is a hydrogen or a methyl radical substituted by the alkyl radicals $R^9$ and $R^{10}$;
$R^4$ is a hydrogen, a methyl radical or an acyloxy radical of the general formula

O—CO—$R^1$ wherein $R^1$ has the abovementioned meaning;
$R^5$, $R^6$, $R^7$, $R^8$ and $R^{10}$ are identical or different and is a hydrogen or methyl;
$R^9$ is a hydrogen and
$R^4$ and $R^9$ can together represent a single carbon bond or a methylene or an ethylene bridge, with the proviso that
  i) in the case of cyclohexyl esters in which $R^1$=methyl, $R^2$=isopropyl, $R^5$=methyl and $R^6$=hydrogen, the substituents $R^2$ and $R^5$ are arranged in a cis relationship to each other;
  ii) in the case of cyclohexyl esters in which $R^2$=isopropenyl, $R^5$=methyl and $R^6$=hydrogen, the substituent $R^1$ is an alkyl group with at least two C atoms;
  iii) in the case of acyclic monofunctional esters, the substituent $R^1$ is an alkyl group with at least two C atoms; and
  iv) in the case of cyclohexyl esters in which $R^2$, $R^7$, $R^8$=hydrogen and $R^5$, $R^6$, $R^{10}$=methyl, the substituent $R^1$ is methyl, ethyl, propyl or 1-propen-1-yl.

It is surprising that it is those esters which only have a very slight inherent odor, which are highly suitable for use as neutralizers of malodors. This applies, in particular, to propionates, isobutyrates and crotonates.

It is also surprising that isomenthyl acetate has a superior neutralizing effect to menthyl acetate already described in this connection (Examples 2 and 4). It is also surprising that bifunctional esters such as, for example, the diacetates, dipropionates etc., obtainable by the derivation of diols, are suitably excellent for use as neutralizers.

Esters which are particularly suitable for neutralizing malodors are, for example,
2,4-dimethyl-3-pentyl propionate;
2,4-dimethyl-3-pentyl isobutyrate;
2,4-dimethyl-3-pentyl crotonate;
2,4-dimethyl-3-pentyl butyrate;
2,6-dimethyl-4-heptyl propionate;
2,6-dimethyl-4-heptyl isobutyrate;
2,6-dimethyl-4-heptyl crotonate;
2,6-dimethyl-4-heptyl butyrate;
3,3,5-trimethylcyclohexyl acetate;
3,3,5-trimethylcyclohexyl propionate;
3,3,5-trimethylcyclohexyl crotonate;
3,3,5-trimethylcyclohexyl butyrate;
menthyl propionate;
menthyl isobutyrate;
menthyl crotonate;
menthyl butyrate;
isomenthyl acetate;
isomenthyl propionate;
isomenthyl isobutyrate;
isomenthyl crotonate;
isomenthyl butyrate;
isopulegyl propionate;
isopulegyl isobutyrate;
isopulegyl crotonate;
isopulegyl butyrate;
2,6,6-trimethylcycloheptyl acetate;
2,6,6-trimethylcycloheptyl propionate;
2,6,6-trimethylcycloheptyl isobutyrate;
2,6,6-trimethylcycloheptyl crotonate;
2,6,6-trimethylcycloheptyl butyrate;
2,2,4-trimethyl-1,3-pentanediyl diacetate;
2,2,4-trimethyl-1,3-pentanediyl dipropionate;
2,2,4-trimethyl-1,3-pentanediyl diisobutyrate;
2,2,4-trimethyl-1,3-pentanediyl dicrotonate;
2,2,4-trimethyl-1,3-pentanediyl dibutyrate;
2-methyl-2,4-pentanediyl diacetate;
2-methyl-2,4-pentanediyl dipropionate;
2-methyl-2,4-pentanediyl diisobutyrate;
2-methyl-2,4-pentanediyl dicrotonate;
2-methyl-2,4-pentanediyl dibutyrate.

2,4-Dimethyl-3-pentyl acetate and 2,6-dimethyl-4-heptyl acetate are not suitable for use as neutralizers due to their powerful inherent odor.

The property of neutralizing malodors applies to all the isomeric forms, i.e., diastereomers and enantiomers, of the above-mentioned esters.

New esters are 2,4-dimethyl-3-pentyl propionate, 2,4-dimethyl-3-pentyl crotonate, 2,4-dimethyl-3-pentyl butyrate, 2,6-dimethyl-4-heptyl propionate, 2,6-dimethyl-4-heptyl isobutyrate, 2,6-dimethyl-4-heptyl crotonate, 2,6-dimethyl-4-heptyl butyrate, isomenthyl isobutyrate, isomenthyl crotonate, isomenthyl butyrate, isopulegyl crotonate, 2-methyl-2,4-pentanediyl dicrotonate and 2.2.4-trimethyl-1,3-pentanediyl dicrotonate.

The preparation of the above-mentioned esters is known per se. They can, for example, be prepared by standard reactions (cf. Vogel's Textbook of Practical Organic Chemistry, 5$^{th}$ Ed., Longman Scientific and Technical, 1989, pp. 698 et seq.), as follows:

The alcohols are reacted with the corresponding carboxylic acid halides or anhydrides in the presence of a basic compound such as for example, pyridine, optionally with heating. If tertiary alcohol groups are to be esterified, 4-N,N-dimethylaminopyridine is added as a catalyst.

In order to combat malodors, the esters according to the present invention can be used in pure form, in mixtures with each other, in suitable solvents such as, for example, ethanol, isopropanol, diethylene glycol monoethyl ether, glycerol, propylene glycol, 1,2-butylene glycol, dipropylene glycol, 2-methyl-2,4-pentanediol, diethyl phthalate, triethyl citrate, isopropyl myristate, benzyl benzoate etc. or together with other nonvolatile materials which have the effect of lowering the vapor pressure of more volatile compounds and are therefore, also suitable for combating malodors, such as, for example, resin esters, modified resin esters; diterpene alcohols, modified diterpene alcohols, polydiols, modified polydiols, etc. They can be excellently combined with perfumes, of which, in particular, those are preferred which, according to the above-definition, represent harmonizing or odor-masking compounds, which are also capable of reducing malodors.

The odor neutralizers according to the present invention generally contain 0.1% to 100% by weight, and preferably 1% to 50 by weight, of the esters, based on the total weight of the odor neutralizer. A content of 5% to 40% by weight, based on the total content of the odor neutralizer, is particularly preferred.

In odor neutralizers, the esters according to the present invention can be combined with fragrances. The fragrances may be compounded from ingredients as can be found, for example, in S. Arctander, Perfume and Flavor Materials, Vols. I and II, Monclair, N. N., 1969, Selbstverlag or K. Bauer, D. Garbe and H. Surburg, Common Fragrances and Flavor Materials, 3$^{rd}$ Ed., Wiley-VCH, Weinheim 1997.

The following may be mentioned as examples of fragrance ingredients, in particular:
extracts from natural raw materials such as essential oils, concretes, absolutes, resins, resinoids, balsams, tinctures such as for example ambergris tincture; amyris oil; angelica seed oil; angelica root oil; aniseed oil; valerian oil; basil oil; tree moss absolute; bay oil; armoise oil; benzoe resinoid; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oakmoss absolute; elemi oil; estragon oil; eucalyptus citriodora oil; eucalyptus oil (cineole type); fennel oil; fir needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon-grass oil; lovage oil; lime oil distilled; lime oil expressed; linaloe oil; Litsea cubeba oil; laurel leaf oil; mace oil; marjoram oil; mandarin oil; massoi (bark) oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil;

peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil: spike-lavender oil; star anise oil; storax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniperberry oil; wine lees oil; wormwood oil; wintergreen oil; ylang-ylang oil; hyssop oil; civet absolute; cinnamon leaf oil; cinnamon bark oil; and fractions thereof or ingredients isolated therefrom;

individual fragrance ingredients from the group comprising hydrocarbons, such as for example 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols, such as for example hexanol; octanol; 3-octanol; 2,6-dimethyl-heptanol; 2-methyl-2-heptanol, 2-methyl-2-octanol; (E)-2-hexenol; (E)- and (Z)-3-hexenol; 1-octen-3-ol; a mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; aliphatic aldehydes and their acetals such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal-diethylacetal; 1,1-dimethoxy-2,2,5-trimethyl-4-hexene; citronellyl oxyacetaldehyde;

aliphatic ketones and oximes thereof, such as for example 2-heptanone; 2-octanone; 3-octanone; 2-nonanone; 5-methyl-3-heptanone; 5-methyl-3-heptanone oxime; 2,4,4,7-tetramethyl-6-octen-3-one; aliphatic sulfur-containing compounds, such as for example 3-methylthiohexanol; 3-methylthiohexyl acetate; 3-mercaptohexanol; 3-mercaptohexyl acetate; 3-mercaptohexyl butyrate; 3-acetyltbiohexyl acetate; 1-menthene-8-thiol; aliphatic nitriles, such as for example 2-nonenenitrile; 2-tridecenenitrile; 2,12-tridecenenitrile; 3,7-dimethyl-2,6-octadienenitrile; 3,7-dimethyl-6-octenenitrile;

aliphatic carboxylic acids and esters thereof, such as for example (E)- and (Z)-3-hexenylformate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexylbutyrate; (E)- and (Z)-3-hexenyl isobutyrate; hexyl crotonate; ethylisovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate;

acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl -5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; α-sinensal; β-sinensal; geranylacetone; as well as the dimethyl- and diethylacetals of geranial, neral and 7-hydroxy-3,7-dimethyloctanal;

cyclic terpene alcohols, such as, for example, menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates of alpha-terpineol; terpinen-4-ol; methan-8-ol; methan-l-ol; methan-7-ol; borneol; isoborneol; linalool oxide; nopol; cedrol; ambrinol; vetiverol; guaiol;

cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-danascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; acetylated cedarwood oil (cedryl methyl ketone);

cyclic alcohols, such as, for example, 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols, such as, for example, alpha,3,3-trimethylcyclo-hexyl-methanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers, such as, for example, cineole; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methyl-propyl)-1,3-dioxan;

cyclic ketones, such as, for example, 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclo-hexanone; 4-tert.-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadeca-none;

cycloaliphatic aldehydes, such as, for example, 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl)ketone;

esters of cyclic alcohols, such as, for example, 2-tert.-butylcyclohexyl acetate; 4-tert.-butylcyclohexyl acetate; 2-tert.-pentylcyclohexyl acetate; 4-tert.-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexa-hydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

esters of cycloaliphatic carboxylic acids, such as, for example, allyl 3-cyclohexyl-propionate; allyl cyclohexyl oxyacetate; methyl dihydrojasmo-nate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; araliphatic ethers, such as for example 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene-dioxybenzaldehyde; 3,4-dimethoxybenzaldehyde; 2-methyl-3-(4-methoxyphenyl)propanal; 2-methyl-3-(4-methylendioxyphenyl)propanal;

aromatic and araliphatic ketones, such as, for example, acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methyl-ethyl)-1H-5-indenyl] ethanone; 5',6',7',8'-tetrahydro-3',5',5',6',8',8'-hexamethyl-2-acetonaphthone;

aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

Nitrogen-containing aromatic compounds, such as, for example, 2,4,6-trinitro-1,3-dimethyl-5-tert-butylbenzene; 3,5-dinitro-2,6-dimethyl-4-tert.-butylacetophenone; cinnamonitrile; 5-phenyl-3-methyl-2-pentenonitrile; 5-phenyl-3-methylpentanonitrile; methyl anthranilate; methy-N-methylanthranilate; Schiff's bases of methyl anthranilate with 7-hydroxy-3,7-dimethyloctanal, 2-methyl-3-(4-tert.-butylphenyl)-propanal or 2,4-dimethyl-3-cyclohexene carbaldehyde; 6-isopropylquinoline; 6-isobutylquinoline; 6-sec.-butylquinoline; indole; skatole; 2-methoxy-3-isopropyl-pyrazine; 2-isobutyl-3-methoxypyrazine;

phenols, phenyl ethers and phenyl esters, such as, for example, estragole; anethole; eugenol; eugenyl methyl ether; isoeugenol; isoeugenol methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

In addition, the odor neutralizers containing the esters according to the present invention can be adsorbed onto a carrier which ensures both the fine distribution of the perfumes in the product and controlled release during use. Such carriers can be porous inorganic materials such as light sulfate, silica gels, zeolites, gypsums, clays, granulated clays, aerated concrete etc. or organic materials such as wood and cellulose-based materials.

The odor neutralizers containing the esters according to the present invention can also be in microencapsulated or spray-dried form or in the form of inclusion complexes or extrusion products and they can be added in this form to the product whose odor is to be improved or which is to be perfumed.

Possibly, the properties of the odor neutralizers modified in the above manner can be further optimized by so-called "coating" with suitable materials for the purpose of the more systematic release of the fragrance concerned, for which purpose, waxlike plastics such as, for example, polyvinyl alcohol are preferably used.

The microencapsulation of the odor neutralizers can, for example, be carried out by the so-called coacervation process with the aid of capsule materials of, for example, polyurethane-like materials or soft gelatins. Spray-dried odor neutralizers can for example be prepared by spray-drying an emulsion or dispersion containing the composition, it, being possible to use modified starches, proteins, dextrin and vegetable gums as the carriers. Inclusion complexes can be prepared, for example, by introducing dispersions of the composition and cyclodexrins or urea derivatives into a suitable solvent, such as for example water. Extrusion products can be prepared by melting the odor neutralizers with a suitable waxlike substance and by extrusion followed by solidification, optionally in a suitable solvent, such as for example isopropanol.

If the odor-neutralizing esters are combined in odor neutralizers with fragrances or single fragrance ingredients, the content of the esters according to the present invention can be between 0.01 and 99% by weight, preferably between 0.2 and 50% by weight, based on the total weight of the odor neutralizer; a content of from 0.5 to 40% by weight, based on the total weight of the odor neutralizer, is particularly preferred.

The invention also relates to the use of esters of the formula

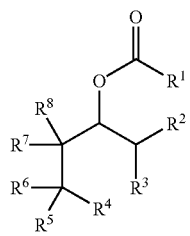

as odor neutralizers, wherein
$R^1$ is an alkyl radical with 1 to 4 carbon atoms which can optionally contain a double bond;
$R^2$ is a hydrogen or an alkyl radical with 1 to 3 carbon atoms which can optionally contain a double bond;
$R^3$ is a hydrogen or a methyl radical substituted by the alkyl radicals $R^9$ and $R^{10}$;
$R^4$ is a hydrogen, a methyl radical or an acyloxy radical of the general formula

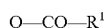 O—CO—$R^1$ wherein $R^1$ has the abovementioned meaning;
$R^5$, $R^6$, $R^7$, $R^8$ and $R^{10}$ are identical or different and is a hydrogen or methyl;
$R^9$ is a hydrogen and
$R^4$ and $R^9$ can together represent a single carbon bond or a methylene or an ethylene bridge,
with the proviso that
i) in the case of cyclohexyl esters in which $R^1$=methyl, $R^2$=isopropyl, $R^5$=methyl and $R^6$=hydrogen, the substituents $R^2$ and $R^5$ are arranged in a cis relationship to each other;

ii) in the case of cyclohexyl esters in which $R^2$=isopropenyl, $R^5$=methyl and $R^6$=hydrogen, the substituent $R^1$ is an alkyl group with at least two C atoms;
iii) in the case of acyclic monofunctional esters, the substituent $R^1$ is an alkyl group with at least two C atoms, and
iv) in the case of cyclohexyl esters in which $R^2$, $R^7$, $R^8$=hydrogen and $R^5$, $R^6$, $R^{10}$=methyl, the substituent $R^1$ is methyl, ethyl, propyl or 1-propen-1-yl.

The odor neutralizers comprising the esters according to the present invention can be used in concentrated form, in solutions or in the above-described modified form in many articles of daily use, such as, for example, for the production of a large number of products, such as, for example, perfume extracts, eaux de parfum, eaux de toilette, aftershaves, eaux de cologne, preshave products, splash colognes and perfumed tissue wipes and for perfuming acidic, alkaline and neutral cleansing agents, such as, for example, floor cleaners, window cleaning agents, washing-up liquids, cleaning agents for bathrooms and sanitary ware, liquid abrasives, solid and liquid toilet cleaners, toilet sticks, powdered and foam-forming carpet cleaners, liquid detergents, powdered detergents, pre-wash agents, such as bleaching agents, soaking agents and stain-removing agents, fabric softeners, laundry soaps, laundry tablets, disinfectants, surface disinfectants, and for perfuming air fresheners in liquid or gel form or in a form applied to a solid substrate, and in particular, for deodorizing exhaust air from air-conditioning systems and industrial processes: as well as for perfuming air fresheners in the form of aerosol or pump sprays, waxes and polishes such as furniture polishes, floor waxes, shoe creams, starching, impregnating or deodorizing textile-treating agents, diapers, sanitary towels, panty liners and body-care products, such as, for example, solid and liquid soaps, shower gels, shampoos, shaving soaps, shaving foams, bath oils, wet wipes, cosmetic emulsions of the oil-in-water, water-in-oil and water-in-oil-in-water type, such as, for example, skin creams and lotions, face creams and lotions, sun protection creams and lotions, aftersun creams and lotions, hand creams and lotions, foot creams and lotions, depilatory creams and lotions, aftershave creams and lotions, tanning creams and lotions, hair care products, such as, for example, hair sprays, hair gels, hair-setting lotions, hair rinses, permanent and semi-permanent hair dyes, hair-forming agents such as cold wave and hair straightening agents, hair tonics, hair creams and lotions, deodorants and antiperspirants such as, for example, axillary sprays, roll-ons, deodorant sticks, deodorant creams, decorative cosmetic products such as, for example, eye-shadows, nail varnishes, make-ups, lipsticks, mascaras, as well as candles, lamp oils, joss-sticks, insecticides, repellents, liquid and gaseous fuels, heating oils and heating gases.

When using the odor neutralizers comprising the esters according to the present invention in the above-mentioned products, the content of the composition can be 0.01 to 40% by weight, preferably 0.05 to 20% by weight, based on the total weight of the product. In many end products, the content of perfume oil can be reduced by 10 to 50%, based on the quantity of the perfume oil employed, as a result of the use of odor neutralizers.

The invention is further illustrated but is not intended to be limited by the following examples in which all parts and percentages are by weight unless otherwise specified.

EXAMPLES

Example 1

Production of the Esters for the Odor Neutralizers According to the Present Invention General Method:

1 mol equivalent of the alcohol to be esterified and 1.5 mol equivalents, or, in the case of diols, 3 mol equivalents, of pyridine are initially introduced into a suitable solvent such as for example toluene or methyl tert.-butyl ether. If tertiary alcohol groups are to be esterified, 0.01 mol equivalent of 4-dimethylaminopyridine is added. 1.2 mol equivalents, or, in the case of diols, 2.4 mol equivalents, of the anhydride or the chloride of the corresponding carboxylic acid are then added at 0° C. When the addition is complete the mixture is stirred at room temperature or with heating, until the reaction has ended. The progress of the reaction is monitored by gas chromatography. Working up is carried out by diluting with water, washing the organic phase with dilute sodium hydroxide solution, hydrochloric acid and soda solution, followed by evaporation. The residue is distilled.

The following esters were prepared by this method:

2,4-dimethyl-3-pentyl propionate:
  m/z=129 ($M^+$–43; 18); 83 (10); 57 (100); 41 (18);

2,4-dimethyl-3-pentyl isobutyrate:
  m/z=143 ($M^+$–43; 27); 83 (23); 71 (100); 57 (39); 43 (96); 41 (51);

2,4-dimethyl-3-pentyl crotonate:
  m/z=141 ($M^+$–43; 10); 69 (100); 41 (28);

2,4-dimethyl-3-pentyl butyrate:
  m/z=143 ($M^+$–43; 12); 83 (13); 71 (100); 57 (14); 43 (40); 41 (14);

2,6-dimethyl-4-heptyl propionate:
  m/z=143 ($M^+$–57; 12); 126 (5); 69 (12); 57 (100); 41 (19);

2,6-dimethyl-4-heptyl isobutyrate:
  m/z=157 ($M^+$–57; 7); 126 (8); 85 (12); 71 (100); 57 (22); 43 (85);

2,6-dimethyl-4-heptyl crotonate:
  m/z=155 ($M^+$–57; 4); 126 (8); 69 (100); 56 (10); 41 (28);

2,6-dimethyl-4-heptyl butyrate:
  m/z=157 ($M^+$–57; 10); 126 (9); 85 (7); 71 (100); 56 (14); 43 (37);

3,3,5-trimethylcyclohexyl acetate:
  m/z=124 ($M^+$–60; 50); 109 (100); 95 (18); 82 (30); 68 (40); 43 (66);

3,3,5-trimethylcyclohexyl propionate:
  m/z=124 ($M^+$–74; 50); 109 (100); 95 (20); 82 (24); 69 (28); 41 (28);

3,3,5-trimethylcyclohexyl isobutyrate:
  m/z=124 ($M^+$–88; 48); 109 (100); 95 (22); 83 (26); 69 (62); 43 (48);

3,3,5-trimethylcyclohexyl crotonate:
  m/z=210 ($M^+$; <1); 141 (2); 124 (35); 109 (76); 69 (100); 41 (62);

3,3,5-trimethylcyclohexyl butyrate:
  m/z=124 ($M^+$–88; 52); 109 (100); 95 (26); 82 (29); 69 (26); 55 (13); 43 (27).

menthyl propionate:
  m/z=138 ($M^+$–74; 34); 123 (20); 95 (64); 81 (53); 57 (100); 41 (46);

menthyl isobutyrate:
  m/z=138 ($M^+$–88; 82); 123 (35); 95 (100); 83 (68); 81 (60); 71 (57); 55 (37); 43 (82);

menthyl crotonate:
  m/z=138 ($M^+$–86; 38); 123 (16); 95)32); 81 (30); 69 (100); 41 (54);

menthyl butyrate:
  m/z=138 ($M^+$–88; 57); 123 (25); 95 (74); 81 (41); 71 (100); 43 (66);

isomenthyl acetate:
  m/z=138 ($M^+$–60; 75); 123 (38); 95 (100); 81 (66); 43 (86);

isomenthyl propionate:
  m/z=138 ($M^+$–74; 34); 123 (20); 95 (64); 81 (53); 57 (100); 41 (46);

isomenthyl isobutyrate:
  m/z=138 ($M^+$–88; 82); 123 (35); 95 (100); 83 (68); 81 (60); 71 (57); 55 (37); 43 (82);

isomenthyl crotonate:
  m/z=138 ($M^+$–86; 38); 123 (16); 95)32); 81 (30); 69 (100); 41 (54);

isomenthyl butyrate:
  m/z=138 ($M^+$–88; 57); 123 (25); 95 (74); 81 (41); 71 (100); 43 (66);

isopulegyl propionate:
  m/z=210 ($M^+$; 1); 136 (45); 121 (30); 107 (23); 93 (26); 81 (31); 57 (100); 41 (20);

isopulegyl isobutyrate:
  m/z=224 ($M^+$; 1); 136 (60); 121 (30); 107 (24); 93 (28); 81 (14); 69 (100); 41 (28);

isopulegyl crotonate:
  m/z=222 ($M^+$; 1); 136 (40); 121 (15); 107 (11); 93 (13); 81 (38); 71 (77); 43 (100);

isopulegyl butyrate:
  m/z=224 ($M^+$; 2); 136 (54); 121 (33); 107 (24); 93 (29); 81 (30); 71 (100); 43 (62);

2,6,6-trimethylcycloheptyl acetate:
  m/z=138 ($M^+$–60; 17); 123 (26); 109 (12); 95 (19); 87 (19); 82 (12); 69 (33); 55 (15); 43 (100);

2,6,6-trimethylcycloheptyl propionate:
  m/z=197 ($M^+$–15; <1); 168 (3); 138 (25); 123 (33); 109 (20); 95 (24); 81 (16); 69 (32); 57 (100);

2,6,6-trimethylcycloheptyl isobutyrate:
  m/z=183 ($M^+$–43; 2); 155 (5); 138 (23); 123 (30); 95 (40); 83 (32); 71 (100); 55 (34); 43 (78);

2,6,6-trimethylcycloheptyl crotonate:
  m/z=209 ($M^+$–15; <1); 153 (5); 138 (14); 123 (18); 95 (32); 83 (25); 69 (100); 55 (15); 41 (28);

2,6,6-trimethylcycloheptyl butyrate:
  m/z=182 ($M^+$–44; 6); 138 (64); 123 (41); 109 (52); 95 (22); 81 (22); 71 (100); 55 (21); 43 (37);

2,2,4-trimethyl-1,3-pentanediyl diacetate:
  m/z=124 ($M^+$–74; 37); 109 (100); 95 (20); 82 (24); 69 (28); 57 (42); 41 (28);

2,2,4-trimethyl-1,3-pentanediyl dipropionate:
  m/z=215 (M$^+$–43; 4); 159 (18); 131 (10); 57 (100);

2,2,4-trimethyl-1,3-pentanediyl diisobutyrate:
  m/z=243 (M$^+$–43; 10); 173 (8); 159 (16); 143 (6); 111 (14); 71 (100); 56 (10); 43 (52);

2,2,4-trimethyl-1,3-pentanediyl dicrotonate:
  m/z=239 (M$^+$–43; 5); 155 (10); 69 (100); 41 (18);

2,2,4-trimethyl-1,3-pentanediyl dibutyrate:
  m/z=243 (M$^+$–43; 5); 173 (15); 159 (10); 111 (8); 71 (100); 56 (8); 43 (28);

2-methyl-2,4-pentanediyl diacetate:
  m/z=187 (M$^+$–15; <1); 145 (4); 101 (12); 85 (23); 83 (26); 59 (16); 43 (100);

2-methyl-2,4-pentanediyl dipropionate:
  m/z=225 (M$^+$–15; <1); 131 (7); 115 (9); 100 (7); 85 (17); 83 (52); 57 (100); 43 (12);

2-methyl-2,4-pentanediyl diisobutyrate:
  m/z=243 (M$^+$–15; 1); 171 (9); 129 (6); 83 (100); 71 (73); 55 (19); 43 (61);

2-methyl-2,4-pentanediyl dicrotonate:
  m/z=239 (M$^+$–15; 5); 169 (7); 155 (5); 125 (4); 99 (8); 83 (35); 69 (100); 55 (8); 41 (20);

2-methyl-2,4-pentanediyl dibutyrate:
  m/z=243 (M$^+$–15; 1); 171 (4); 129 (4); 99 (5); 83 (70); 71 (100); 55 (16); 43 (49).

Example 2

Testing the Odor Neutralizers According to the Present Invention for their Activity Against Sweat Malodor a) An artificial sweat malodor was prepared by mixing the following components (all values represent parts by weight):

| | |
|---|---|
| 1% butyric acid in diethyl phthalate | 5 |
| 1% isovaleric acid in diethyl phthalate | 10 |
| 1% caproic acid in diethyl phthalate | 15 |
| 1% 3-heptyloxyacetic acid in diethyl phthalate | 10 |
| 1% 3-methyl-2-hexenoic acid in diethyl phthalate | 20 |
| 1% phenylacetic acid in diethyl phthalate | 0.5 |
| 1% thioglycolic acid in diethyl phthalate | 5 |
| skatole | 0.1 |
| diethyl phthalate | 34.4 |
| total | 100 | b) A test solution was prepared from 4 g of the above-described artificial sweat malodor, 20 g of Triton X100 and 76 g of water. 0.5 g of this test solution was poured drop by drop onto a wad of cotton wool which was placed in a 120 ml beaker. 0.05 g of the substance to be tested for its odor-neutralizing activity was applied to a second wad of cotton wool in the same beaker. The beaker was sealed with a lid and left to stand overnight. The odor of the gas phase which had formed above the two wads of cotton wool was assessed by a panel of organoleptically trained experts. The reference standard used was a beaker containing only one wad of cotton wool onto which only the sweat malodor test solution had been applied. The intensity of the malodor of the standard was given a rating of 8 on a scale ranging from 0 (odorless) to 10 (extremely odorous) and its total odor intensity a rating of 8 on a scale ranging from 0 to 10. As shown in Table 1, the organoleptic panel assessed whether the unpleasant note of the test mixture was reduced or enhanced by the addition of the substance to be tested and whether the total odor intensity was decreased or increased as a result of the substance to be tested. The following esters displayed satisfactory neutralizing properties, i.e. the property of reducing the malodor of sweat, without significantly increasing the total odor intensity:

TABLE 1

| Compound | Reduction in the intensity of the malodor [units of intensity] | Increase/reduction in the total odor intensity [units of intensity] |
|---|---|---|
| 2,2,4-trimethyl-1,3-pentanediyl dicrotonate | 1 | 0 |
| 2-methyl-2,4-pentanediyl diacetate | 1 | 0 |
| 2,6-dimethyl-4-heptyl crotonate | 7 | 0 |
| 2,6-dimethyl-4-heptyl isobutyrate | 1 | 0 |
| 2,6-dimethyl-4-heptyl propionate | 2 | 0 |
| 2,4-dimethyl-3-pentyl crotonate | 6 | 0 |
| 2,6,6-trimethylcycloheptyl acetate | 5 | 0 |
| 2,6,6-trimethylcycloheptyl propionate | 4 | 0 |
| 2,4-dimethyl-3-pentyl propionate | 4 | 0 |
| isomenthyl acetate | 4 | –3 |
| menthyl acetate (standard) | 3 | –1 |
| menthyl crotonate | 3 | –1 |
| 3,3,5-trimethylcyclohexyl acetate | 4 | 1 |
| 3,3,5-trimethylcyclohexyl crotonate | 2 | 0 |

Example 3

Testing the Odor Neutralizers According to the Present Invention for Their Activity Against an Ammonia Malodor 50 mg of the substance to be tested were added to 10 g of a non-perfumed hair dye containing about 8% of a 35% ammonia solution in a 120 ml beaker and mixed. The odor of the resulting gas phase was assessed by a panel of experts in comparison with the gas phase of a beaker containing only the hair dye.

The intensity of the malodor of the standard was given a rating of 9 on a scale ranging from 0 (odorless) to 10 (extremely odorous). As shown in Table 2, the organoleptic panel assessed whether the unpleasant note of the test mixture was reduced or enhanced by the addition of the substance to be tested and whether the total odor intensity decreased or increased as a result of the substance to be tested.

The following esters displayed satisfactory neutralizing properties, i.e., a capacity for reducing the malodor of ammonia without themselves having any significantly noticeable odor intensity:

TABLE 2

| Compound | Reduction in the intensity of the malodor [units of intensity] | Increase in the total odor intensity [units of intensity] |
|---|---|---|
| 2,6-dimethyl-4-heptyl propionate | 1 | 0 |
| 2,6-dimethyl-4-heptyl crotonate | 3 | 0 |
| 2,2,4-trimethyl-1,3-pentanediyl acetate | 4 | 1 |
| 2,2,4-trimethyl-1,3-pentanediyl propionate | 1 | 0 |

Example 4

Testing the Esters According to the Present Invention for Their Activity Against a Tobacco Smoke Malodor 35 wads of cotton wool were placed in a 1 l beaker and exposed to tobacco smoke for 30 minutes. In each case, one of the wads of cotton wool thus treated was placed in a 120 ml beaker. 5 μl of the substance to be tested for its odor-neutralizing activity was applied to an additional wad of cotton wool in the same beaker. The odor of the gas phase which had formed above the two wads of cotton wool was assessed by a panel of organoleptically trained experts. The reference standard used was a beaker containing only one wad of cotton wool treated with tobacco smoke. The intensity of the malodor of the standard was given a rating of 7 on a scale ranging from 0 (odorless) to 10 (extremely odorous). The total odor intensity on a corresponding scale was also given a rating of 7. As shown in Table 3, the organoleptic panel assessed whether the unpleasant note of the test mixture was reduced or enhanced by the addition of the substance to be tested and whether the total odor intensity was reduced or increased by the substance to be tested.

The following esters displayed satisfactory neutralizing properties, i.e., the property of reducing the malodor of tobacco smoke, without significantly increasing the total odor intensity:

TABLE 3

| Compound | Reduction in the intensity of the malodor [units of intensity] | Increase/reduction in the total odor intensity [units of intensity] |
|---|---|---|
| 2,2,4-trimethyl-1,3-pentanediyl acetate | 2 | 0 |
| 2,2,4-trimethyl-1,3-pentanediyl dicrotonate | 2 | 0 |
| 2-methyl-2,4-pentanediyl diacetate | 5 | 1 |
| 2,6-dimethyl-4-heptyl isobutyrate; | 2 | −2 |
| 2,6-dimethyl-4-heptyl propionate; | 2 | −1 |
| 2,4-dimethyl-3-pentyl crotonate; | 6 | 1 |
| 2,4-dimethyl-3-pentyl isobutyrate; | 4 | 0 |
| 2,4-dimethyl-3-pentyl propionate; | 2 | −1 |
| 2,6,6-trimethylcycloheptyl acetate | 5 | 1 |
| 2,6,6-trimethylcycloheptyl propionate | 3 | −2 |
| isomenthyl acetate | 6 | −2 |
| menthyl acetate (standard) | 1 | 0 |
| menthyl crotonate | 4 | −1 |
| 3,3,5-trimethylcyclohexyl acetate; | 5 | 1 |
| 3,3,5-trimethylcyclohexyl crotonate; | 5 | 1 |
| 3,3,5-trimethylcyclohexyl propionate | 4 | −1 |

Example 5

Testing the Odor Neutralizers According to the Present Invention for Their Activity Against Bathroom Malodor An artificial bathroom malodor was prepared by mixing the following components in accordance with Example 13 of U.S. Pat. No. 4,719,105 (all the values represent parts by weight):

| | |
|---|---|
| dipropylene glycol | 62.82 |
| skatole | 0.91 |
| beta-thionaphthol | 0.91 |
| mercaptoacetic acid | 21.18 |
| caproic acid | 6 |
| p-cresylphenyl acetate | 2.18 |
| N-methyl morpholine | 6 |
| Total | 100 |

A 0.5% aqueous test solution was prepared from the bathroom malodor thus prepared. 0.1 g of this test solution was poured drop by drop onto a wad of cotton wool which was placed in a 120 ml beaker. 5 μl of the substance to be tested for its odor-neutralizing effect was applied to an additional wad of cotton wool in the same beaker. The beaker was sealed with a lid and left to stand overnight. The odor of the gas phase, which had formed above the two wads of cotton wool was assessed by a panel of organoleptically trained panel experts. The reference standard used was a beaker containing only one wad of cotton wool to which the bathroom malodor test solution had been applied. The intensity of the malodor of the standard was given a rating of 8 on a scale ranging from 0 (odorless) to 10 (extremely odorous) and the total odor intensity of the standard was also given a rating of 8 on a corresponding scale of 0 to 10. As shown in Table 4, the organoleptic panel assessed whether the unpleasant note of the test mixture was reduced or increased by the addition of the substance to be tested and whether the total odor intensity was reduced or increased by the substance to be tested.

The following esters displayed satisfactory neutralizing properties, i.e. the property of reducing the malodor of feces, urine, etc. without significantly increasing the total odor intensity:

TABLE 4

| Compound | Reduction in the intensity of the malodor [units of intensity] | Increase/reduction in the total odor intensity [units of intensity] |
|---|---|---|
| 2,4-dimethyl-3-pentyl crotonate | 4 | 0 |
| 2,4-dimethyl-3-pentyl propionate | 2 | 0 |
| 3,3,5-trimethylcyclohexyl acetate | 2 | −1 |
| 3,3,5-trimethylcyclohexyl crotonate | 2 | −1 |
| 3,3,5-trimethylcyclohexyl propionate | 2 | −1 |
| 2,6,6-trimethylcycloheptyl propionate | 1 | −1 |

Example 6

Testing the Odor Neutralizers According to the Invention for Their Activity Against Kitchen Malodors An artificial kitchen malodor was prepared by mixing the following components (all values represent parts by weight):

| | |
|---|---|
| artificial chicken aroma | 2 |
| artificial tomato aroma | 1.5 |
| artificial cooking fat aroma | 3 |
| trimethylamine | 1 |
| onion oil | 2 |
| garlic oil | 3 |
| ethanol | 87.5 |
| total | 100 |

A 0.001% aqueous test solution was prepared from the artificial kitchen malodor thus prepared. 0.5 g of this test solution was poured drop by drop onto a wad of cotton wool which was placed in a 120 ml beaker. 5 µl of the substance to be tested for its odor-neutralizing activity was applied to an additional wad of cotton wool in the same beaker. The beaker was sealed with a lid and left to stand overnight. The odor of the gas phase which had formed above the two wads of cotton wool was assessed by a panel of organoleptically trained experts. The reference standard used was a beaker containing only one wad of cotton wool to which only the kitchen malodor test solution had been applied. The intensity of the malodor of the standard was given a rating of 7 on a scale ranging from 0 (odorless) to 10 (extremely odorous). The total odor intensity was also given a rating of 7 on a corresponding scale from 0 to 10. As shown in Table 5, the organoleptic panel assessed whether the unpleasant note of the test mixture was reduced or enhanced by the addition of the substance to be tested and whether the total odor intensity was reduced or increased by the substance to be tested.

The following esters displayed satisfactory neutralizing properties, i.e., the property of reducing unpleasant kitchen malodors without significantly increasing the total odor intensity:

TABLE 5

| Compound | Reduction in the intensity of the malodor [units of intensity] | Increase/reduction in the total odor intensity [units of intensity] |
| --- | --- | --- |
| 2-methyl-2,4-pentanediyl diacetate | 3 | 0 |
| 2,6-dimethyl-4-heptyl isobutyrate | 2 | −2 |
| 2,4-dimethyl-3-pentyl propionate | 1 | 0 |
| 2,6,6-trimethylcycloheptyl acetate | 3 | −1 |
| menthyl acetate (standard) | 3 | 0 |
| 3,3,5-trimethylcyclohexyl acetate | 2 | 0 |
| 3,3,5-trimethylcyclohexyl propionate | 2 | −1 |

Example 7

Preparation of a Composition for Neutralizing Malodors in Wet Wipes

The following components are mixed together: 30 parts by weight of dipropylene glycol, 25 parts by weight of menthyl isobutyrate, 15 parts by weight of isopropyl myristate; 15 parts by weight of triethyl citrate and 15 parts by weight of benzyl benzoate. With the aid of an emulsifier, a 0.05% aqueous solution is prepared from this composition and used for treating the wet wipes. The treated wet wipes have a considerably more neutral odor than non-treated wet wipes. The characteristic odor of wet cardboard has disappeared.

Example 8

Preparation of a Composition for Neutralizing Tobacco Smoke Malodors on Textiles The following components are mixed together: 20 parts by weight of dipropylene glycol, 25 parts by weight of 2,4-dimethyl-3-pentyl crotonate, 15 parts by weight of isopropyl myristate; 15 parts by weight of triethyl citrate, 5 parts by weight of benzyl benzoate and 20 parts by weight of a perfume oil consisting of a mixture of odor-harmonizing fragrances. A water-based aerosol spray containing 1% of this composition is sprayed onto net curtains having a powerful tobacco smoke odor. After spraying, the net curtains have a considerably more neutral odor and the unpleasant tarry smoke odor has disappeared. Similar effects can be obtained if the odor-neutralizing composition is sprayed onto other textiles such as items of clothing and furniture upholstery.

Example 9

Preparation of a Composition for Neutralizing Kitchen Malodors on Textiles

The following components are mixed together: 30 parts by weight of dipropylene glycol, 25 parts by weight of 2,6-dimethyl-4-heptyl isobutyrate, 15 parts by weight of isopropyl myristate; 15 parts by weight of triethyl citrate, 10 parts by weight of benzyl benzoate and 5 parts by weight of a perfume oil consisting of a mixture of odor-harmonizing fragrances. A water-based aerosol spray containing 1% of this composition is sprayed onto net curtains or items of clothing having a powerful kitchen odor of fried onions and hot cooking fat. After spraying, the net curtains have a considerably more neutral odor. The unpleasant, fatty, onion odor has disappeared.

Example 10

The Preparation of a Composition for Neutralizing Urine Malodors in Diapers

The following components are mixed together: 25 parts by weight of isomenthyl acetate, 30 parts by weight of isopropyl myristate; 30 parts by weight of triethyl citrate and 15 parts by weight of benzyl benzoate. This composition is converted with the aid of the INCAP® (A trademark of Haarmann & Reimer GmbH, Holzminden) system into a microencap-sulated form containing about 50% of this composition.

The microcapsules are placed between two layers of paper bonded at the edges and incorporated into a paper diaper. On coming into contact with moisture, the odor-neutralizing composition is released and considerably reduces the emerging urine odor compared with non-treated diapers.

Example 11

The Preparation of a Composition for Neutralizing the Malodor of a Washing Powder Raw Material The following components are mixed together: 20 parts by weight of dipropylene glycol, 25 parts by weight of 2,2,4-trimethyl-1,3-pentanediyl dipropionate, 15 parts by weight of isopropyl myristate; 15 parts by weight of triethyl citrate, 5 parts by weight of benzyl benzoate and 20 parts by weight of a mixture of odor-harmonizing perfumes. A 0.3% solution of this composition is sprayed onto the washing powder. After spraying, the odor becomes considerably more neutral and the fatty rancid odor disappears.

Example 12

Preparation of a Composition for Neutralizing Bathroom Malodors

The following components are mixed together: 20 parts by weight of dipropylene glycol, 25 parts by weight of 2,4-dimethyl-3-pentyl crotonate, 15 parts by weight of isopropyl myristate, 15 parts by weight of triethyl citrate and 15 parts by weight of benzyl benzoate. 1% of this composition and 4% of a perfume oil composition having a fresh-coniferous odor are incorporated into a toilet stick. For comparison purposes, 5% of the pure perfume oil composition are incorporated into another toilet stick. In order to test the specimens, odor chambers of a size of 2.5 m³ are filled with an artificial bathroom malodor (cf. Example 5) The toilet sticks are hooked onto the toilet bowls located in the odor chambers. After actuating the flush the quality of the air in the chamber is evaluated after 30 minutes by a panel of experts. The toilet sticks containing the odor-neutralizing composition produced a considerably more neutral odor impression. The characteristic odor of the perfume oil was more clear and distinct. Similar effects can be obtained with the odor-neutralizing composition and perfume oils of the flowery or citrus fresh type.

Example 13

Preparation of a Composition for Neutralizing Bathroom Malodors

The following components are mixed together: 30 parts by weight of dipropylene glycol, 25 parts by weight of 3,3,5-trimethylcyclohexyl propionate, 15 parts by weight of isopropyl myristate; 15 parts by weight of triethyl citrate and 15 parts by weight of benzyl benzoate. 2.5% of this composition and 7.5% of a perfume oil composition with a fresh citrus odor are incorporated into air fresheners of the stearate or carrageenan type. For comparison purposes, 10% of the pure perfume oil composition are incorporated into another air freshener. For test purposes, odor chambers measuring 2.5 m³ are filled with an artificial bathroom malodor (cf. Example 5). After placing the air fresheners in the chambers, the quality of the air is evaluated by a panel of experts. The air fresheners containing the odor-neutralizing composition produced a significantly more neutral odor impression. The characteristic odor of the perfume is more clear and distinct.

Example 14

Use of Isomenthyl Acetate for Neutralizing the Malodor of a Fabric Softener Product A fabric softener base prepared from 70 parts by weight of demineralized water, 0.25 parts by weight of concentrated hydrochloric acid, 1 part by weight of calcium chloride dihydrate, 0.5 parts by weight of Polysorbat 20 and 27 parts by weight of Varisoft 315 (Witco), was mixed with 1.25 parts by weight of a perfume oil. By adding 0.05 parts by weight of isomenthyl acetate, the odor of the finished product becomes considerably more neutral, and the product has an altogether more clean and fresh odor.

Example 15

Use of Isomenthyl Acetate for Neutralizing the Malodor of Cat's Urine

A perfume oil containing 30% of isomenthyl acetate is sprayed, while mixing, onto cat litter material consisting of bentonite in a concentration of 0.1 parts by weight of perfume oil per 1000 parts by weight of bentonite. For comparison purposes, the same perfume oil without isomethyl acetate is applied in the same concentration. After adding cat's urine, it is found that the cat litter material treated only with perfume oil unsatisfactorily reduced the malodor of cat's urine, whereas, in contrast, the cat's litter material containing the additional isomenthyl acetate had a relatively neutral odor and thus, considerably reduced the malodor caused by the highly odorous cat's urine.

Example 16

Preparation of an Underarm Spray for Neutralizing Sweat Malodor

The following components are mixed together: 30 parts by weight of dipropylene glycol, 25 parts by weight of isomethyl acetate, 15 parts by weight of isopropyl myristate; 15 parts by weight of triethyl citrate and 15 parts by weight of benzyl benzoate. A fat-restoring deodorant spray is prepared from 0.5 parts by weight of this composition, 40 parts by weight of 80% alcohol, 1 part by weight of perfume oil, 3 parts by weight of isopropyl myristate and 55 parts by weight of a propellant (a propane/butane mixture). For comparison purposes, a spray of the same composition, which does not contain any odor-neutralizing composition, but 1.5 parts by weight of perfume oil, is prepared. On spraying onto the axillary area it is found that the spray containing the odor-neutralizing composition reduces unpleasant sweat malodor considerably more effectively and the fragrance of the perfume is even more pronounced.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An odor neutralizer comprising at least one ester selected from the group consisting of:
    isomenthyl isobutyrate;
    isomenthyl crotonate;
    isomenthyl butyrate; and
    isomenthyl propionate.

2. An odor neutralizer formulated to reduce at least one malodor selected from the group consisting of sweat, urine, feces, tobacco, waste, molds, sulfur and amines as well as kitchen odors, wherein said odor neutralizer is at least one ester selected from the group consisting of:
    isomenthyl isobutyrate;
    isomenthyl crotonate;
    isomenthyl butyrate; and
    isomenthyl propionate.

3. A personal care product comprising a cosmetic or daily health care product of daily use and an odor neutralizer comprising at least one ester selected from the group consisting of:
    isomenthyl isobutyrate;
    isomenthyl crotonate;
    isomenthyl butyrate; and
    isomenthyl propionate.

4. A perfumed product comprising at least one fragrance ingredient and at least one odor neutralizer selected from the group consisting of:
    isomenthyl isobutyrate;
    isomenthyl crotonate;
    isomenthyl butyrate; and
    isomenthyl propionate.

5. A cleaning product comprising at least one cleansing agent and an odor neutralizer selected from the group consisting of:
    isomenthyl isobutyrate;
    isomenthyl crotonate;
    isomenthyl butyrate; and
    isomenthyl propionate.

6. A method for neutralizing a malodor, wherein said malodor is selected from the group consisting of sweat, urine, feces, tobacco, waste, molds, sulfur and amines as well as kitchen odors, wherein said method comprises applying to said malodor at least one ester selected from the group consisting of:

isomenthyl acetate;

isomenthyl isobutyrate;

isomenthyl crotonate;

isomenthyl butyrate; and isomenthyl propionate.

* * * * *

UNITED STATES PATENT AND TRADEMARK OFFICE
CERTIFICATE OF CORRECTION

PATENT NO. : 7,157,411 B2  
APPLICATION NO. : 10/149564  
DATED : January 2, 2007  
INVENTOR(S) : Rohde et al.

Page 1 of 1

It is certified that error appears in the above-identified patent and that said Letters Patent is hereby corrected as shown below:

Column 5, line 58, replace "2.2.4-trimethyl-1," with -- 2,2,4-trimethyl-1, --

Column 7, line 4, replace "celery seed oil:" with -- celery seed oil; --

Column 7, line 39 & 40, replace "3-acetylt-biohexyl acetate;" with -- 3-acetylthiohexyl acetate --

Column 7, line 63, replace "3,7-dimethyl-1,5,7-octatrien-3-ol 2,6-dimethyl-2,5,7-" with -- 3,7-dimethyl-1,5,7-octatrien-3-ol; 2,6-dimethyl-2,5,7- --

Column 8, line 22, replace "beta-danascenone;" with -- beta-damascenone --

Column 14, line 9, replace "95)32);" with -- 95(32); --

Column 14, line 27, replace "95)32);" with -- 95(32); --

Signed and Sealed this

Fourth Day of November, 2008

JON W. DUDAS  
*Director of the United States Patent and Trademark Office*